(12) United States Patent
Stenzler et al.

(10) Patent No.: US 9,949,873 B2
(45) Date of Patent: Apr. 24, 2018

(54) HEAT RETENTION MASK AND METHOD OF USING THE SAME

(71) Applicant: 12th Man Technologies, Inc., Garden Grove, CA (US)

(72) Inventors: Alex Stenzler, Long Beach, CA (US); Steve Han, Huntington Beach, CA (US); Mei-Sheng Teng, Kowloon (HK)

(73) Assignee: 12th Man Technologies, Inc., Garden Grove, CA (US)

( * ) Notice: Subject to any disclaimer, the term of this patent is extended or adjusted under 35 U.S.C. 154(b) by 119 days.

(21) Appl. No.: 13/938,899

(22) Filed: Jul. 10, 2013

(65) Prior Publication Data

US 2014/0014101 A1   Jan. 16, 2014

Related U.S. Application Data

(60) Provisional application No. 61/670,281, filed on Jul. 11, 2012.

(51) Int. Cl.
*A62B 7/10*      (2006.01)
*A61F 7/00*      (2006.01)
(Continued)

(52) U.S. Cl.
CPC .............. *A61F 7/0085* (2013.01); *A61F 7/00* (2013.01); *A61F 7/02* (2013.01); *A62B 7/10* (2013.01);
(Continued)

(58) Field of Classification Search
CPC .. A61M 16/00; A61M 15/00; A61M 16/1045; A61M 16/1075; A62B 15/00; A62B 7/02; A62B 17/005; A62B 7/10; A61G 12/00; A61F 7/0085; A61F 7/02; A61F 2007/0257; A61F 2007/0006; A61F 2007/0003; A61F 2007/0018; A61F 2007/0061; A61F 7/00
(Continued)

(56) References Cited

U.S. PATENT DOCUMENTS 2,551,142 A * 5/1951 Lessard .................... A61F 7/02
126/204
3,139,885 A * 7/1964 Hirtz .................... A61M 15/00
128/203.27
(Continued)

*Primary Examiner* — Kathryn E Ditmer
(74) *Attorney, Agent, or Firm* — Riverside Law LLP

(57) ABSTRACT

A device and method for reducing heat loss in at least one region of a subject's body is described. The device includes a mask component, a heat releasing reservoir, and a conduit connecting the mask component to the heat releasing reservoir and creating an airflow path therethrough, wherein the heat releasing reservoir includes at least one air permeable region that is impermeable to condensed water. Heat loss is reduced by the subject positioning the mask over the mouth and/or nose, positioning the heat releasing reservoir over the region of the subject's body, and passing warmed air exhaled by the subject into the mask through the conduit and into the heat releasing reservoir, such that the warmed air passes through the heat releasing reservoir while retaining condensed water within the heat releasing reservoir, thereby increasing the temperature of the air surrounding the at least one region of the subject's body.

17 Claims, 4 Drawing Sheets

(51) Int. Cl.
  *A62B 17/00* (2006.01)
  *A61F 7/02* (2006.01)
(52) U.S. Cl.
  CPC .... *A62B 17/005* (2013.01); *A61F 2007/0003* (2013.01); *A61F 2007/0006* (2013.01); *A61F 2007/0061* (2013.01); *A61F 2007/0257* (2013.01)
(58) Field of Classification Search
  USPC ........... 128/201.13, 204.17, 203.22, 203.26, 128/206.11, 206.15, 206.21; 126/204; 607/108, 114, 112, 104, 96; 165/46; 219/211
  See application file for complete search history.

(56) References Cited

U.S. PATENT DOCUMENTS

| | | | | |
|---|---|---|---|---|
| 3,153,720 A * | 10/1964 | Petronio | ............ | A41D 13/0051 128/DIG. 23 |
| 3,229,681 A * | 1/1966 | Gluckstein | ......... | A41D 13/0051 126/204 |
| 3,491,754 A * | 1/1970 | Weese | ...................... | 128/204.17 |
| 3,707,966 A * | 1/1973 | Nebel | ...................... | 128/204.17 |
| 3,902,486 A * | 9/1975 | Guichard | ................. | 128/203.22 |
| 3,910,780 A * | 10/1975 | Henley | ................. | B01D 53/22 128/205.28 |
| 4,015,294 A * | 4/1977 | O'Neill | ................... | B63C 11/06 2/421 |
| 4,062,359 A * | 12/1977 | Geaghan | ........... | A61M 16/1075 128/203.12 |
| 4,492,228 A * | 1/1985 | Makovic | ........... | A61M 16/1075 128/207.17 |
| 4,683,869 A * | 8/1987 | Wilcox | ........................ | 126/204 |
| 5,029,572 A * | 7/1991 | LeBlanc | ........... | A41D 13/0025 126/204 |
| 5,490,501 A * | 2/1996 | Crowley | .............. | A63B 29/021 128/200.24 |
| 5,976,176 A * | 11/1999 | Webb, II | ................... | A61F 7/00 607/104 |
| 6,600,086 B1 * | 7/2003 | Mace et al. | .................... | 604/369 |
| 6,807,964 B1 * | 10/2004 | Ruddy | ............. | A61M 16/1075 128/201.13 |
| 2001/0006173 A1 * | 7/2001 | Rock | ........................ | D04B 1/04 219/545 |
| 2003/0164170 A1 * | 9/2003 | Drew | .................... | A61M 16/06 128/204.18 |
| 2003/0168063 A1 * | 9/2003 | Gambone et al. | ....... | 128/203.16 |
| 2004/0102124 A1 | 5/2004 | Suzuki | | |
| 2006/0174392 A1 * | 8/2006 | Farnworth | ......... | A41D 13/0025 2/102 |
| 2006/0212103 A1 | 9/2006 | Wagner, III | | |
| 2007/0113853 A1 * | 5/2007 | Pavesi | .................... | A62B 9/003 128/205.25 |
| 2007/0131229 A1 * | 6/2007 | Madaus | ................ | A61M 16/06 128/206.21 |
| 2008/0268765 A1 * | 10/2008 | Luvera | ............... | A41D 13/0051 454/230 |
| 2012/0240935 A1 * | 9/2012 | Johansen | .......... | A61M 16/0045 128/205.17 |

* cited by examiner

HEAT RETENTION MASK AND METHOD OF USING THE SAME

CROSS-REFERENCE TO RELATED APPLICATIONS

This application claims priority to U.S. provisional application Ser. No. 61/670,281 filed Jul. 11, 2012, the entire disclosure of which is incorporated by reference herein in its entirety.

BACKGROUND OF THE INVENTION

Small changes in environmental temperature can significantly alter comfort levels. For hospital patients, as well as for campers, military personnel or even the homeless caught or subjected to cold environments, maintaining a comfortable environmental temperature may be critical to health or ability to sleep. Even a 2 to 3 degree change in temperature can alter the sense of comfort by a subject. Currently, items such as heated blankets, hot air blowers or hot water mattresses are required to raise the surrounding temperature in these environments.

Unfortunately, it is often the case that a subject does not have such equipment available to them, or it is not practical for a subject to carry such equipment. Therefore, there is a need in the art for a heat retention device and system that efficiently utilizes the warmer temperature of exhaled breath to help maintain body heat and/or reduce heat loss. The present invention satisfies this need.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION

It is to be understood that the figures and descriptions of the present invention have been simplified to illustrate elements that are relevant for a clear understanding of the present invention, while eliminating, for the purpose of clarity, many other elements found in heat retention systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform, make or use the disclosed invention.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Figure 1:
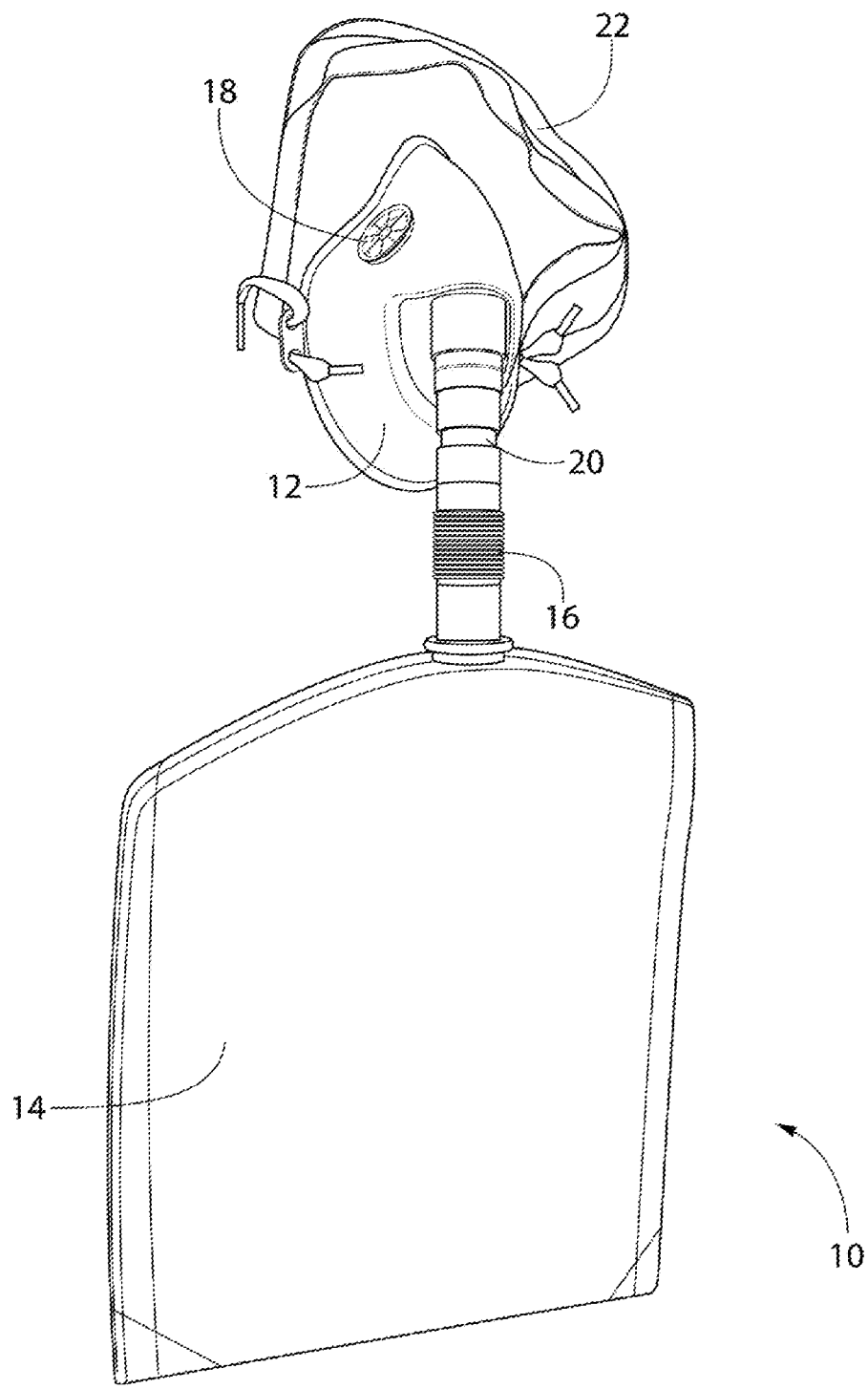
FIG. 1 is a photograph of a first embodiment of the present invention, where the inspiratory valve is positioned within the mask wall and an expiratory valve is in the tube leading to the heat releasing reservoir.
Figure 2:
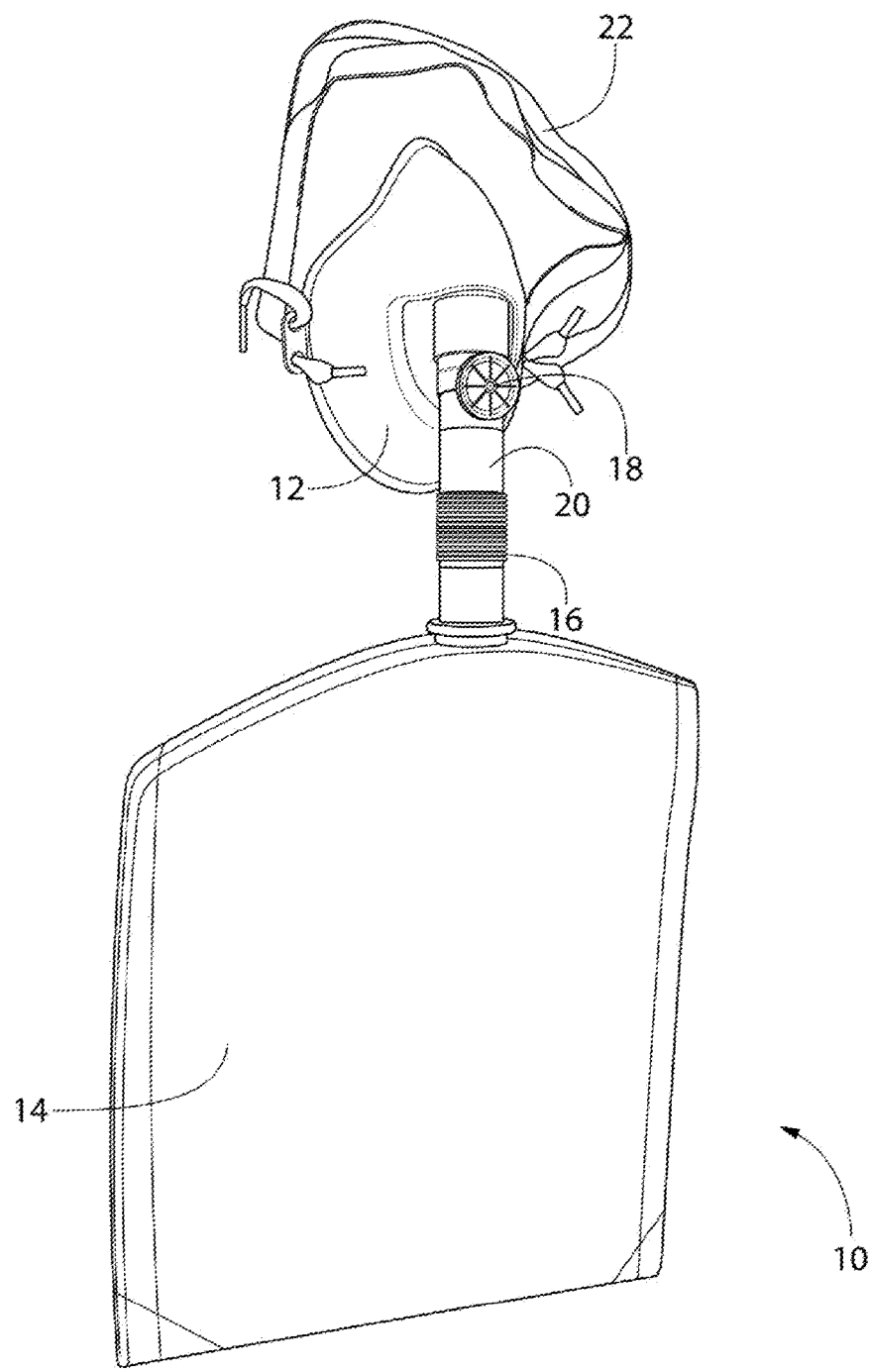
FIG. 2 is a photograph of a second embodiment of the present invention, where the inspiratory and expiratory valves are positioned within the connecting tube.
Figure 3:
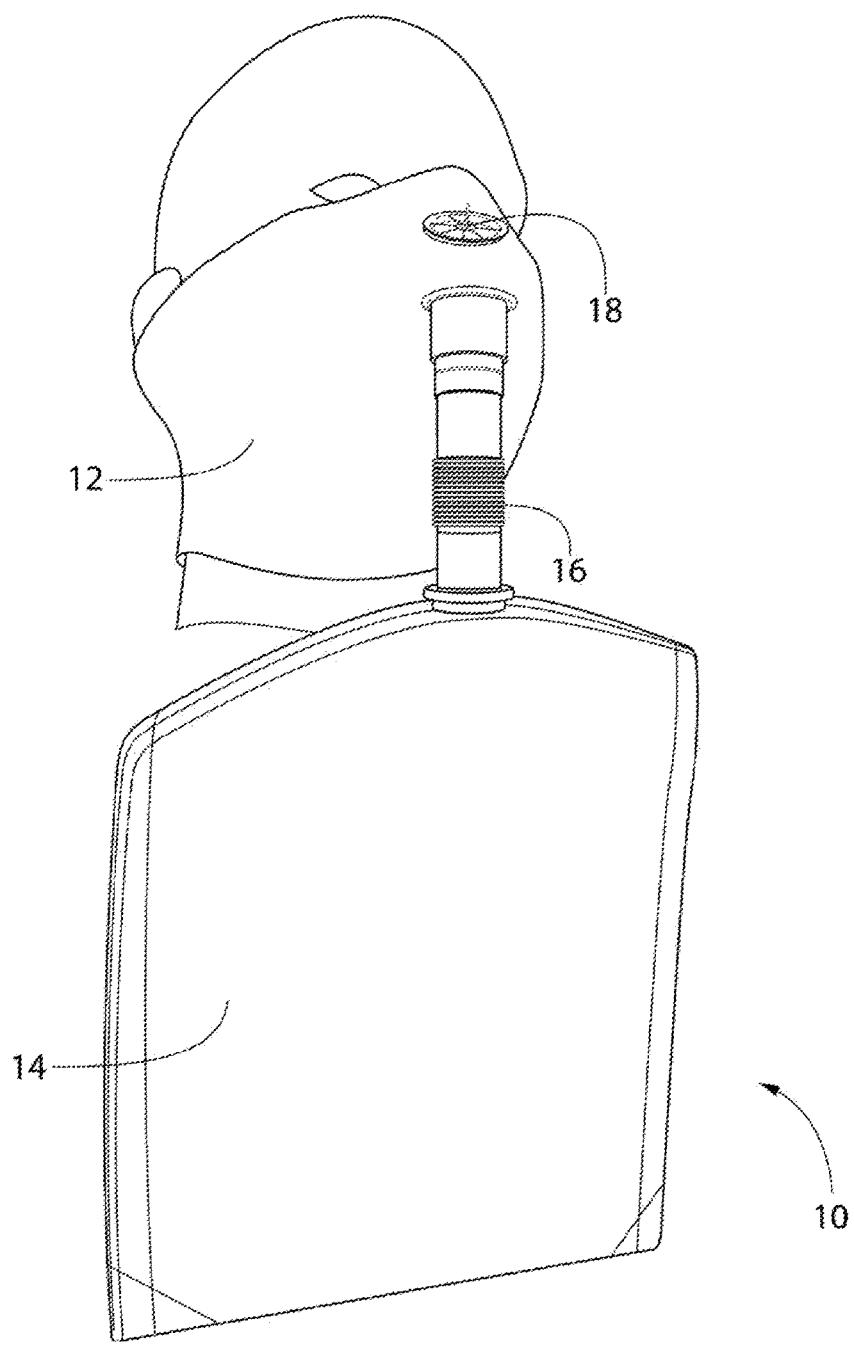
FIG. 3 is a photograph of a third embodiment of the present invention suitable for colder climates, where the mask component is composed of neoprene and both the inspiratory and expiratory valves are positioned within the mask.

As described herein, the present invention relates to a device, system and method for retaining heat, or maintaining heat, in a subject. For example, as generally shown in FIGS. 1-3, the device 10 includes a mask component 12, a heat releasing reservoir 14, a connecting tube or conduit 16 connecting the mask component 12 to the heat releasing reservoir 14, and one or more inspiratory/expiratory valves 18, 20 positioned within the mask component, connecting tube or both. As contemplated herein, when a subject places the mask component 12 over the mouth and/or nose, the subject can inhale air, warm the air within the subject's body, exhale the warmed air into the heat releasing reservoir 14, which releases the warmed air adjacent to the heat releasing reservoir 14. In some embodiments, the mask component, connecting tube and heat releasing reservoir are fixedly attached, such that the device forms a single, integrated unit. In other embodiments, one or more components may be releasably attached, such that the integrated device may have detachable and/or replaceable components.

As contemplated herein, the mask component 12 may include full-face coverage, or partial coverage of either or both the nose and mouth, as would be understood by those skilled in the art. For example, the mask component may generally resemble and conform to the subject's face in a manner similar to an oxygen mask, aerosol mask or venturi mask, including any mechanism 22 for securing the mask to the subject's face (standard tie strings, elastic bands, etc.) as would be understood by those skilled in the art. The mask component may be reusable, autoclavable and/or disposable, and may be composed of standard materials such as rubber, silicone, plastic or other polymeric material, or even cloth. For colder weather applications, the mask component may be composed of or additionally include neoprene, as is shown in FIG. 3. Preferably, the mask component will be impermeable to air, thereby requiring exhaled air to pass through an expiratory valve into the connecting tube and ultimately into the heat releasing reservoir. The mask component may be molded such that it includes an extension for securing the connecting tube to the mask, or it may include a connecting port for releasably securing the connecting tube into the mask.

The connecting tube 16 may also be composed of rubber, silicone, plastic or other polymeric material. The connecting tube serves as a conduit between the mask component and the heat releasing reservoir, and therefore may be any desired length. The lumen of the connecting tube may be of any diameter, provided that exhaled air can pass through its length and into the heat releasing reservoir. As contemplated herein, the connecting tube may be thermally insulated by any mechanism understood by those skilled in the art, so as to minimize the loss of heat within the exhaled air as it travels to the heat releasing reservoir. For example, the connecting tube may be composed of a thermal insulating material, or the connecting tube may have an additional internal or external insulating layer, liner or covering. Non-limiting examples of such materials and layering include metal foils, rubber, double walled plastics or other polymers, and the like.

The present invention further includes one or more valves 18, 20 to selectively permit the passage of air into and/or out of the device of present invention. The valves may be one-way or two-way as would be understood by those in the art, and may be positioned within the mask component, within the connecting tube, or both the mask and connecting tube. Further, the valve(s) may be positioned as or within a fitting between the mask component and the connecting tube. For example, as shown in FIG. 1, an inspiratory valve 18 is positioned within the mask wall and an expiratory valve 20 is positioned in the connecting tube leading to the heat releasing reservoir. In the embodiment of FIG. 3, an inspiratory valve 18 and an expiratory valve (not shown) are both positioned within the mask component. In still other embodiments, the inspiratory valve 18 and the expiratory valve 20 may both be positioned in the connecting tube, as shown in FIG. 2. As contemplated herein, there is no limitation to the number and type of valves used, provided that air that has been warmed by the body can pass from the mask to the heat releasing reservoir via the connecting tube.

The heat releasing reservoir 14 may resemble a bag of any desired shape, and may be positioned on an area of the subject's body that is to be heated by the present invention, such as the chest, abdomen or any other desired portion of the body. The heat releasing reservoir includes at least one portion that is air permeable, such that the warmed air may be released through the material and onto the subject's body that is in close proximity to the heat releasing reservoir. In certain embodiments, the entire heat releasing reservoir is air permeable. In other embodiments, only the portion of the heat releasing reservoir that is positioned against or in contact with the subject is air permeable. In other embodiments, the heat releasing reservoir may include materials within the heat releasing reservoir that form, in any random arrangement or pattern, internal absorbant layer(s), internal filtering layer(s), and the like.

While the heat releasing reservoir includes at least one region that is air permeable, the reservoir may be impermeable to water. For example, warmed air produced by the subject's breath contains moisture, and as it travels through the mask component and connecting tube to the heat releasing reservoir, water condenses out as the air cools. By being impermeable to water, the heat releasing reservoir retains any condensed water from the subject's exhaled breath, thereby selectively releasing only the warmed air and remaining vapor while the condensed water is captured in the reservoir. Thus, the present invention provides greater heat reduction efficiencies via direct air flow (verses radiant heat), and further reduces unwanted cooling that would otherwise occur from the subject's body being exposed to condensed water. In other embodiments, the heat releasing reservoir may act as a filter that reduces or eliminates microbes or pathogens by capturing them along with any condensed water. This is particularly desirable when used by hospitalized patients who may have an incision on their chest or abdomen, as this would reduce the risk of infection from bacteria in their exhaled breath coming in contact with the wound. Subsequently, water that condenses from the exhaled breath remains within the reservoir and can be emptied or disposed of as needed.

The breathable or air permeable portions of the heat releasing reservoir that are also impermeable to condensed water may be composed of hydrophobic materials, such as woven or non-woven polypropylene, polytetrafluoroethylene (PTFE) or other hydrophobic or absorbent materials. Alternatively, such hydrophobic materials may be applied as a coating to selected regions of the heat releasing reservoir to obtain similar functionality.

The present invention further includes methods of reducing heat loss in a subject, or methods of maintaining or retaining body heat in a subject, using the devices as described herein. As contemplated herein, the subject first inhales external air, warms the inhaled air within the body, and exhales the warmed air into the mask, wherein the warmed air passes through the expiratory valve and ultimately to the heat releasing reservoir, where the warmed air is distributed across the body within the vicinity of the reservoir while at the same time retaining any condensed water, thereby adding warmed air to the surrounding external surface area of the subject and ultimately maintaining or reducing the loss of internal temperature of the subject body or body region.

In certain embodiments, the present invention can increase the temperature of the air surrounding the subject between 0.5 and 10° F. In another example, the present invention can capture between 0.5 and 10 liters per minute of heated air for distribution across the body. By using the subject's own body heat to return heat to the air surrounding the subject's body, the present invention provides a method for retaining or maintaining the subject's body heat, or for reducing the loss of the subject's body heat, without the use of an external energy source, and with a reduced caloric intake by the subject.

The present invention is useful in a variety of applications and settings where retention or maintenance of a subject's body temperature, or the reduction of heat lost by the subject's body, is desired. For example, in a hospital setting, a patient whose health is compromised can use the present invention to increase the temperature of the air surrounding the patient's body without the need for extra blankets. Further, the patient can effectively retain or maintain their own body temperature or increase the localized temperature of the air surrounding a body wound or treatment site without risking the introduction of unwanted microbes or pathogens to the region. Thus, the present invention may be used as an important adjunct to patient temperature management for preoperative hypothermia prevention, mild postoperative hypothermia recovery, and normothermic patient comfort.

In another example, the present invention can be used by campers, military personnel or even a homeless subject who may be exposed to colder climates and without access to secondary heat or energy sources. In such instances, the present invention can be easily carried by the subject along with their other camping or military gear, and used to efficiently retain or maintain their core body temperature, or otherwise reduce the loss of core body heat, to withstand the colder climate.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The purpose of the following experiment was to record the heat retention effects of the present invention as compared with a single cotton bed sheet and a bed sheet supplement with a Mylar rescue blanket.

Test Equipment

The test equipment used included an Omega Omegaette HH303 Dual Channel Digital Thermometer, two Omega K-Type Thermocouples, the heat retention mask of the present invention, a Mylar rescue blanket, a cotton patient gown, a cotton bed sheet and a digital stopwatch.

Initial Assessment Testing

The digital thermometer had two inputs to enable differential temperature monitoring. To assess the precision of the thermocouples, both thermocouples were place next to each other and the temperature readings were compared. Once stable, the two thermocouples remained within +/−0.3 degrees of each other. This simultaneous differential measurement system allowed for variations in room temperature without affecting the interpretation of the results.

Procedure

A volunteer subject donned the patient gown. Lying on a cushioned surface in a room with an environmental temperature of approximately 66° F., one of the thermocouples was taped to the patient gown in the mid-chest region. The second thermocouple was taped to the pillow 5 inches above the subject's head to record environmental temperature.

A bed sheet was placed over the subject's body, covering them to their neck and temperatures from both sensors were recorded at the start, at 5 minutes and at 10 minutes.

The bed sheet was then removed and a Mylar rescue blanket was placed over the subject's body and the sheet replaced. Again, temperatures from both sensors were recorded at the start, at 5 minutes and at 10 minutes.

The subject then put on the heat retention mask, with the heat releasing reservoir over their chest and under the Mylar blanket and bed sheet. Again, temperatures from both sensors were recorded at the start, at 5 minutes and at 10 minutes.

Following this period, the two sensors were placed next to one another and a comparison of the two sensors was performed to assure accurate differential temperatures.

Test Data

Room temperature was measured by both sensors at 65.8±0.5 and the difference between the thermocouples was at all times less the 0.03 degrees.

Table 1 below reflects the temperature recordings with just the bed sheet.

| Time | Room Temperature | Gown Temperature | Differential Temperature |
|---|---|---|---|
| 0 min | 66.3 | 73.1 | 6.8 |
| 5 min | 65.4 | 78.1 | 12.7 |
| 10 min | 65.4 | 78.4 | 13 |

Table 2 below reflects the temperature recordings with the bed sheet and Mylar blanket.

| Time | Room Temperature | Gown Temperature | Differential Temperature |
|---|---|---|---|
| 0 min | 66.4 | 73.1 | 6.6 |
| 5 min | 65.8 | 79.0 | 13.2 |
| 10 min | 65.7 | 78.7 | 13 |

Table 3 below reflects the temperature recordings with the bed sheet. Mylar blanket and the heat retention mask of the present invention.

| Time | Room Temperature | Gown Temperature | Differential Temperature |
|---|---|---|---|
| 0 min | 66.4 | 72.5 | 6.1 |
| 5 min | 66.3 | 80.4 | 14.1 |
| 10 min | 65.6 | 85.2 | 19.6 |

Figure 4:
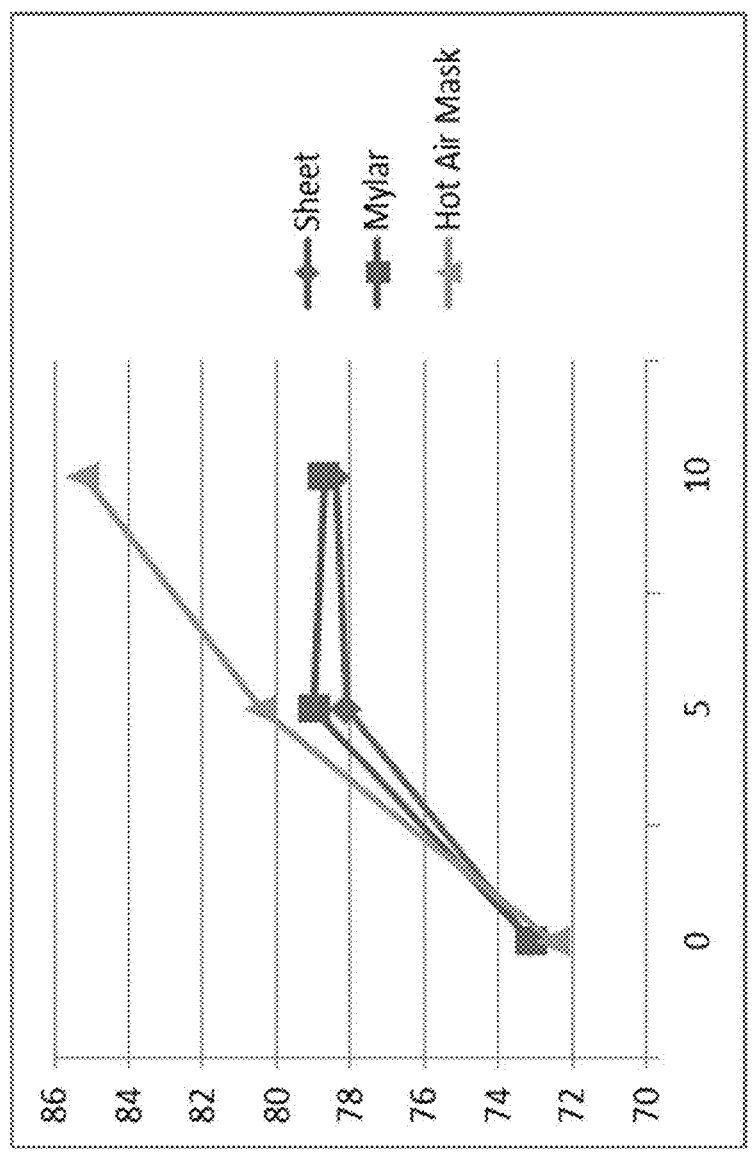
FIG. 4 is a graph depicting the significant increase in temperature of air surrounding a subject using the hot air mask of the present invention than with a bed sheet and/or Mylar rescue blanket alone.

The results of this experiment are further depicted in the graph of FIG. 4.

As demonstrated by the aforementioned experimental example, the heat retention mask of the present invention was able to increase the temperature of the air surrounding the subject greater than just a bed sheet or a Mylar rescue blanket.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A device for reducing heat loss in at least one region of a subject's body, comprising:
    an air impermeable mask component;
    a heat releasing reservoir that is a bag; and
    a single conduit connecting the mask component to the heat releasing reservoir and creating an airflow path for warm exhaled air to pass from the mask to the heat releasing reservoir; and
    a one-way expiratory valve configured to selectively permit the passage of air to flow through the conduit to the heat releasing reservoir;

wherein the device is sized such that the heat releasing reservoir is positionable on a subject's chest or abdomen when the mask is positioned on the subject's face; and wherein the heat releasing reservoir includes a surface having at least one air permeable region that is impermeable to condensed water that permits warm air to pass from the interior of the heat releasing reservoir to the exterior of the heat releasing reservoir surface.

2. The device of claim 1, wherein the at least one air permeable region of the heat releasing reservoir is composed of a hydrophobic material.

3. The device of claim 2, wherein the hydrophobic material is polypropylene or polytetrafluoroethylene (PTFE).

4. The device of claim 1, wherein the mask component includes an inspiratory valve.

5. The device of claim 1, wherein the expiratory valve is positioned in the mask component.

6. The device of claim 1, wherein the expiratory valve is positioned in the conduit.

7. The device of claim 1, wherein the expiratory valve is positioned in a fitting between the mask component and the conduit.

8. The device of claim 1, wherein the heat releasing reservoir filters microbes or pathogens carried in the subject's exhaled air.

9. The device of claim 1, wherein the conduit is thermally insulated.

10. The device of claim 1, wherein the mask component comprises neoprene.

11. The device of claim 1, wherein the mask component is autoclaveable.

12. The device of claim 1, wherein the heat releasing reservoir is detachable from the conduit.

13. The device of claim 1, wherein the mask component is detachable from the conduit.

14. The device of claim 1, wherein the conduit is detachable from both the mask component and the heat releasing reservoir.

15. A method of reducing heat loss in at least one region of a subject's body, comprising:

positioning an air impermeable mask over at least one of the subject's mouth and nose;

positioning a heat releasing reservoir that is a bag over the subject's chest or abdomen, wherein the heat releasing reservoir includes a surface having at least one air permeable region that is impermeable to condensed water, wherein the mask and heat releasing reservoir are connected by a one-way expiratory valve and a single conduit that creates a unidirectional airflow path therethrough; and passing warmed air exhaled by the subject into the mask through the conduit and into the heat releasing reservoir;

wherein the warmed air passes through the air permeable region of the heat releasing reservoir while retaining condensed water within the heat releasing reservoir, thereby increasing the temperature of air surrounding the subject's chest or abdomen.

16. The method of claim 15, wherein the at least one air permeable region of the heat releasing reservoir is composed of a hydrophobic material.

17. The method of claim 16, wherein the hydrophobic material is polypropylene or polytetrafluoroethylene (PTFE).

* * * * *